United States Patent [19]

Slate et al.

[11] Patent Number: 4,919,596
[45] Date of Patent: Apr. 24, 1990

[54] FLUID DELIVERY CONTROL AND MONITORING APPARATUS FOR A MEDICATION INFUSION SYSTEM

[75] Inventors: John B. Slate, Studio City; James L. Henke, Simi Valley, both of Calif.

[73] Assignee: Pacesetter Infusion, Ltd., Sylmar, Calif.

[21] Appl. No.: 344,494

[22] Filed: Apr. 26, 1989

Related U.S. Application Data

[63] Continuation of Ser. No. 128,973, Dec. 4, 1987, abandoned.

[51] Int. Cl.$^5$ .............................................. F04B 23/06
[52] U.S. Cl. ........................................ 417/18; 417/63; 417/415; 417/479; 604/154
[58] Field of Search ................... 417/63, 360, 362, 410, 417/415, 570, 479, 44, 45, 18; 604/65-67, 151-155; 128/DIG. 12, DIG. 13, DIG. 1

[56] References Cited

U.S. PATENT DOCUMENTS

| | | | |
|---|---|---|---|
| 4,236,880 | 12/1980 | Archibald | 417/478 |
| 4,277,226 | 7/1981 | Archibald | 417/38 |
| 4,468,222 | 8/1984 | Lundquist | 604/153 |
| 4,470,758 | 9/1984 | Pazemenas | 417/63 |
| 4,479,761 | 10/1984 | Bilstad et al. | 417/345 |
| 4,493,706 | 1/1985 | Borsanyi et al. | 417/474 |
| 4,573,994 | 4/1986 | Fischell et al. | 604/140 |
| 4,617,637 | 10/1986 | Chu et al. | 364/505 |
| 4,696,671 | 9/1987 | Epstein et al. | 128/DIG. 13 |

Primary Examiner—Leonard E. Smith
Assistant Examiner—David W. Scheuermann
Attorney, Agent, or Firm—Henry M. Bissell; Leslie S. Miller

[57] ABSTRACT

A fluid delivery monitoring and control apparatus for use in a medication infusion system is designed for use with a disposable fluid pathway that incorporates a sterile cassette containing pumping elements and sensor interfaces. The apparatus comprises a multi-segment drive mechanism, controller, and monitoring system. Fluid pumping is accomplished by controlling DC motors in the drive mechanism, each of which is coupled to two valves and a reciprocating piston for an individual pumping channel in the cassette. The motor is geared down to provide an appropriate maximum speed and torque. A cam sequentially actuates an inlet valve, piston, and an outlet valve in the cassette. A range of fluid delivery rates is achieved by periodically sending pulses to the motor. The output flow rate of the pump is maintained by a digital feedback controller which uses closed-loop feedback control to provide accurate regulation. At regular time intervals, the controller computes the motor voltage pulse width based upon feedback information from an encoder.

14 Claims, 3 Drawing Sheets

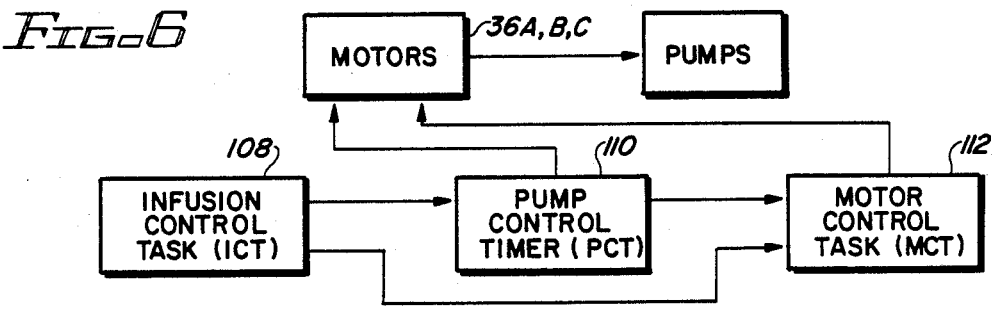

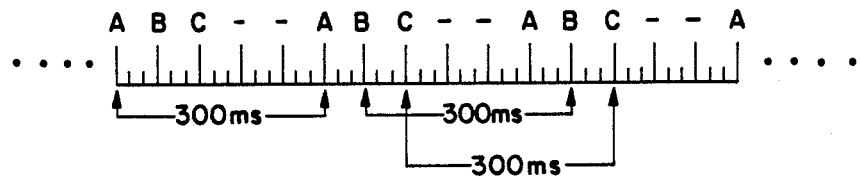

SHORT TICKS INDICATE OPERATING SYSTEM CLOCK INTERVAL (20 MILLISECONDS)
LONG TICKS INDICATE PUMP CONTROL TIMER EXECUTION (60 MILLISECONDS)
A, B, C &- INDICATE WHICH PUMP RECEIVES HANDLING (- INDICATES NULL OPERATION)

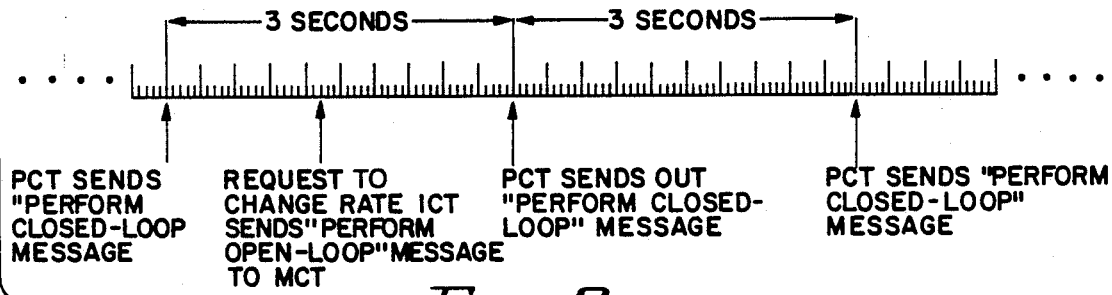

SHORT TICKS INDICATE EXECUTION OF PUMP CONTROL TIMER (60 MILLISEC. INTERVAL)
LONG TICKS INDICATE EXECUTION OF PROCESSING FOR PUMP OF INTEREST (300 MILLISECOND INTERVAL

SHORT TICKS INDICATE EXECUTION OF PUMP CONTROL TIMER (60 MILLISEC. INTERVAL)
LONG TICKS INDICATE EXECUTION OF PROCESSING FOR PUMP OF INTEREST (300 MILLISECOND INTERVAL)

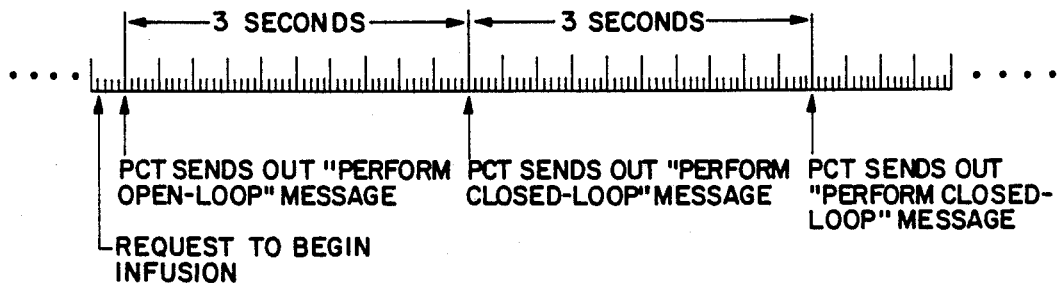

FLUID DELIVERY CONTROL AND MONITORING APPARATUS FOR A MEDICATION INFUSION SYSTEM

This is a continuation of co-pending application application Ser. No. 128,973, filed on Dec. 4, 1987, now abandoned.

This application is related to nine other co-pending patent applications. These patent applications are U.S. Ser. No. 07/127,333, now 4,872,813 issued on Oct. 10, 1989, entitled "Disposable Cassette for a Medication Infusion System," U.S. Ser. No. 07/127,350, entitled "Piston Cap and Boot Seal for a Medication Infusion System," U.S. Ser. No. 07/128,122, now 4,856,340 issued on Aug. 15, 1989, entitled "Pressure Diaphragm for a Medication Infusion System," U.S. Ser. No. 07/128,009, now 4,878,896 issued on Nov. 7, 1989, entitled "Cassette Optical Identification Apparatus for a Medication Infusion System," U.S. Ser. No. 07/128,121, entitled "Air-In-Line Detector for a Medication Infusion System," U.S. Ser. No. 07/127,359, now 4,818,190 issued on Apr. 4, 1989, entitled "Cassette Loading and Latching Apparatus for a Medication Infusion System," U.S. Ser. No. 07/127,133, now 4,850,817 issued on Jul. 25, 1989, entitled "Mechanical Drive System for a Medication Infusion System," all of which were filed Dec. 1, 1987, and U.S. Ser. No. 07/128,966, entitled "Clinical Configuration of Multimode Medication Infusion System," and U.S. Ser. No. 07/128,978, entitled "User Interface for Multimode Medication Infusion System," filed concurrently herewith. All of these applications are assigned to the assignee of this application.

BACKGROUND OF THE INVENTION

The present invention relates generally to an electromechanical system for continuously infusing medication into a patient and, more particularly, to a fluid delivery control and monitoring apparatus used in such a medication infusion system.

Until recently there were two major techniques available for delivering drugs to a patient when the drugs cannot be orally administered. The first technique is to inject the drug into the patient with a syringe and needle to deliver an appreciable dose at relatively infrequent intervals. This technique is not always satisfactory, particularly when the drug being injected is potentially lethal, possibly has undesirable side effects when given in a large dosage, or must be delivered more or less continuously to arrive at a desired therapeutic result. This technique leaves much to be desired. The risks of overdosage or harmful side effects may be reduced by giving smaller injections at more frequent intervals, an inconvenient and not altogether satisfactory alternative.

The need for delivering a drug more or less continuously to achieve a desired therapeutic effect gives rise to the second technique, which involves a continuous delivery of medication to the patient, typically through an intravenous drip. Medication may also be administered using an intravenous system with an injection into a complicated and cumbersome interconnection of IV tubes, hoses, and other components. Drop counters are used to measure the amount of fluid delivered, and medications are often delivered in a large dose through injection into the IV lines, with the medication being somewhat diluted by the fluid.

A relatively recent alternative to these two techniques of administering medication to a patient is the medication infusion pump. A valuable and much needed development, the medication infusion pump can be used to administer drugs to a patient in small, carefully measured doses at frequent intervals or, with some devices, slowly but uninterruptedly. A therapeutic regimen with an infusion pump can be controlled electronically to administer precisely measured quantities of a drug at precisely planned intervals to give a gradual infusion of medication into the patient. The infusion pump makes possible a closer approximation to the natural maintenance of biochemical balances in the body because of its operation in a repetitive small dose.

Disposability is an important consideration in the design of medication infusion systems. Parts of the system through which medication is pumped must be sterile, so that in most applications some of the equipment is used and then discarded. The disposable parts are typically replaced at regular intervals, typically on a daily basis. Disposability of the fluid pump portion of the infusion device is a highly desirable feature. It would be very convenient to design a fluid pump in the form of an attachable cassette of economical design which could easily be installed onto a main pumping unit. A cassette which uses a small number of parts, is easily mass producible, and is capable of delivering liquid medication or other therapeutic fluids with a high degree of precision is described in U.S. patent application Ser. No. 07/127,333 now 4,872,813 issued on Oct. 10, 1989, entitled "Disposable Cassette for a Medication Infusion System." The contents of that application are incorporated herein by reference.

The disposable cassette which is referred to above includes a fluid pump affording a high degree of accuracy in fluid delivery, with the degree of accuracy being maintained throughout the life of the product. The cassette also provides means for conveniently and easily priming the pump, and includes a bubble trap to prevent the frequent shutdowns and alarms which are a problem with presently available pumps. The cassette also includes additional devices such as pressure sensing means and bubble detecting means which in conventional medication infusion systems constitute separate assemblies.

A fluid monitoring and control system for use with disposable cassettes is needed to ensure accurate and safe delivery of therapeutic fluids. The design of such a system requires careful attention to factors involved in the accuracy of fluid delivery, and instrument monitoring functions are necessary to insure safe operation of the system.

There has been a long-felt but unresolved need for the development of a medication infusion management system that can be used for patient care in both hospitals and home health care applications. A desirable system would provide a reliable and improved product for current applications to encourage the use of new therapeutic techniques, reduce the cost of hospitalization by improving care and decreasing labor and inventory costs, and would be versatile enough to allow intra-arterial and subcutaneous infusions. Primary requirements of such a system would be volumetric accuracy, state-of-the-art safety functions, and a capacity for independently controlling more than one pumping channel, each with a separate line to the patient.

Ideally the pump of the medication infusion system would be substantially smaller and lighter than current hospital pumps while at the same time incorporating multiple pumping channels. Together with the possibility of extended battery-powered operation, these features would make a device that is very well suited to ambulatory care, intensive care, emergency transport, emergency care, and operating room use.

A system with the capacity for multiple pumping channels, a variety of disposable configurations, and a library of software functions could combine the capabilities of several currently available devices into one single unit. For example, the need in a hospital for separate syringe pumps, PCA pumps, neonatal pumps, general purpose pumps, and computer communications pumps could be eliminated in favor of one system that could satisfy the requirements for all these devices.

The necessity for cost containment is recognized in the health care industry. Costs can be broken up into three categories: material, labor, and maintenance. With intravenous infusion devices, a major consideration is the cost of disposables, since a large number are required per year. A medication infusion system that keeps down the cost of disposables, is easy to set up, simple to use, and highly reliable would be a great boon to the health care field.

SUMMARY OF THE INvENTION

A fluid delivery monitoring and control apparatus for use in a medication infusion system is provided which has the desirable characteristics described above. The apparatus is designed for use with a disposable fluid pathway that incorporates a sterile cassette containing pumping elements and sensor interfaces in a multi-channel configuration. The apparatus comprises a multiple drive mechanism, controller, and monitoring system. Fluid pumping is accomplished for multiple channels by independently controlling DC motors in the drive mechanism, each of which is coupled to two valves and a reciprocating piston for an individual pumping channel in the cassette. The motor is geared down to provide an appropriate maximum speed and torque. A cam sequentially actuates an inlet valve, piston, and outlet valve in the cassette. Initially the cam is at a "home" position (180°) with the inlet valve open and outlet valve closed, with the pump cylinder ready to be filled. Starting at the home position, the motor rotates the cam at maximum speed, backing the piston to the top of its stroke and thus rapidly filling the cylinder. Next the inlet valve is closed and the outlet valve is opened; having one valve always closed in this manner prevents free-flow. A range of fluid delivery rates is achieved by periodically sending pulses to the motor. At the end of the piston delivery stroke, the motor operates at maximum speed to close the outlet valve and open the inlet valve, thus completing the pumping cycle.

The average flow output of the pump is maintained near the set point rate by a digital feedback controller which uses closed-loop feedback control to provide accurate regulation. This is made necessary because of differences in load parameters created by drive and cassette friction, inertia, and fluid back pressure. At regular time intervals, the controller computes the motor voltage pulse width based upon feedback information from an encoder. Two different pulse amplitude levels are used to provide a range of average flow rates from 0.1 to 999 ml/hr (milliliters per hour), using an 80 $\mu$l stroke volume. The drive speed of the motor is correlated with fluid flow to arrive at a flow rate calibration. Errors in flow rate are minimized by regulating the motor speed accurately.

A drive shaft encoder supplies information necessary for operation of the pump with respect to: (1) a home position; (2) a delivery stroke marker: (3) incremental delivery markers: and (4) a brake marker at the end of the refill cycle. For very small flow rates it is necessary to stop the motor at the end of the refill cycle. This is done by shorting the motor windings during a braking period.

A fluid delivery monitoring system detects conditions which could endanger the patient, such as (1) loss of fluid flow due to an occlusion somewhere in the system; (2) inaccuracy in the volume of fluid delivered greater than a specified amount; (3) infusion of significant amounts of air into the patient; (4) lack of proper latching of the cassette into place; and (5) instrumental malfunction.

In a preferred embodiment three pumping channels are operated independently. The pumping arrangement is modular to simplify construction, testing, and repair and to allow the possibility of providing one- and two-channel versions with common parts. Each pump module comprises a bottom support structure, a drive mechanism, a motor, an anti-backdrive clutch (brake), and an encoder.

BRIEF DESCRIPTION OF THE DRAWINGS

A better understanding of the present invention may be realized from a consideration of the following detailed description, taken in conjunction with the accompanying drawing in which:

FIG. 6 is a schematic block diagram of the fluid delivery control software procedures;

FIG. 7 is a timing diagram for the pump controller;

FIG. 8 is a timing diagram for starting infusion; and

FIG. 9 is a timing diagram for a pumping rate change.

DESCRIPTION OF THE PREFERRED EMBODIMENTS

Figure 1:
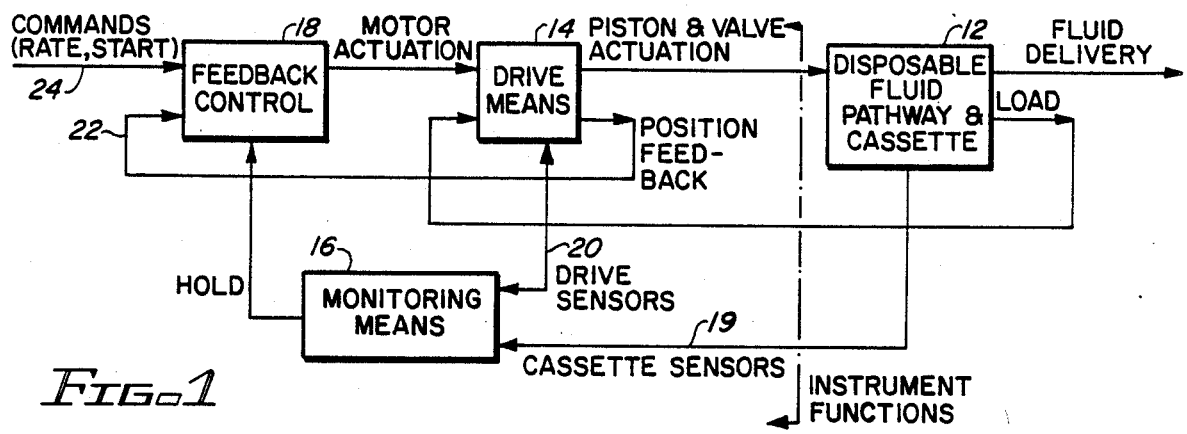
FIG. 1 is a schematic block diagram of the organization of the fluid delivery monitoring and control system.

FIG. 1 shows the overall organization of a fluid delivery monitoring and control apparatus 10 according to the present invention for use in a medication infusion system employing a disposable fluid pathway and cassette 12. Fluid delivery monitoring and control apparatus 10 comprises three major functional blocks: drive means 14, monitoring means 16, and control means 18. Disposable fluid pathway and cassette 12 is described in detail in U.S. patent application Ser. No. 07/127,333, now 4,872,813 issued on Oct. 10, 1989, entitled "Disposable Cassette for a Medication Infusion System." In brief, the disposable cassette has only seven components and utilizes a highly accurate and reliable piston-type fluid pump which employs an active valve design of great accuracy and precision despite its simplicity. A bubble trap is included in the cassette for removing air bubbles which may be introduced into the system by the fluid supply apparatus. The cassette has standard Luer fittings on inlet and outlet tubes. In the preferred embodiment, the cassette also includes both a pressure diaphragm for enabling pressure sensing of the outlet line, and a bubble detector for detecting bubbles in excess of an acceptable size in the fluid supply to a patient.

Drive means 14 actuates one or more pumps contained in the disposable fluid pathway and cassette 12 which effect the delivery of fluid to patient. The outputs of cassette sensors interfacing with the cassette 12 are sent to monitoring means 16 via interconnection path 19. Information from drive sensors in drive means 14 is communicated to monitoring means 16 via interconnection 20. Position feedback information ia sent from drive means 14 to control means 18 by way of path 22. Control means 18 actuates drive means 14 in response to various commands on an input line 24. Control means 18 is also responsive to monitoring means 16.

Figure 2:
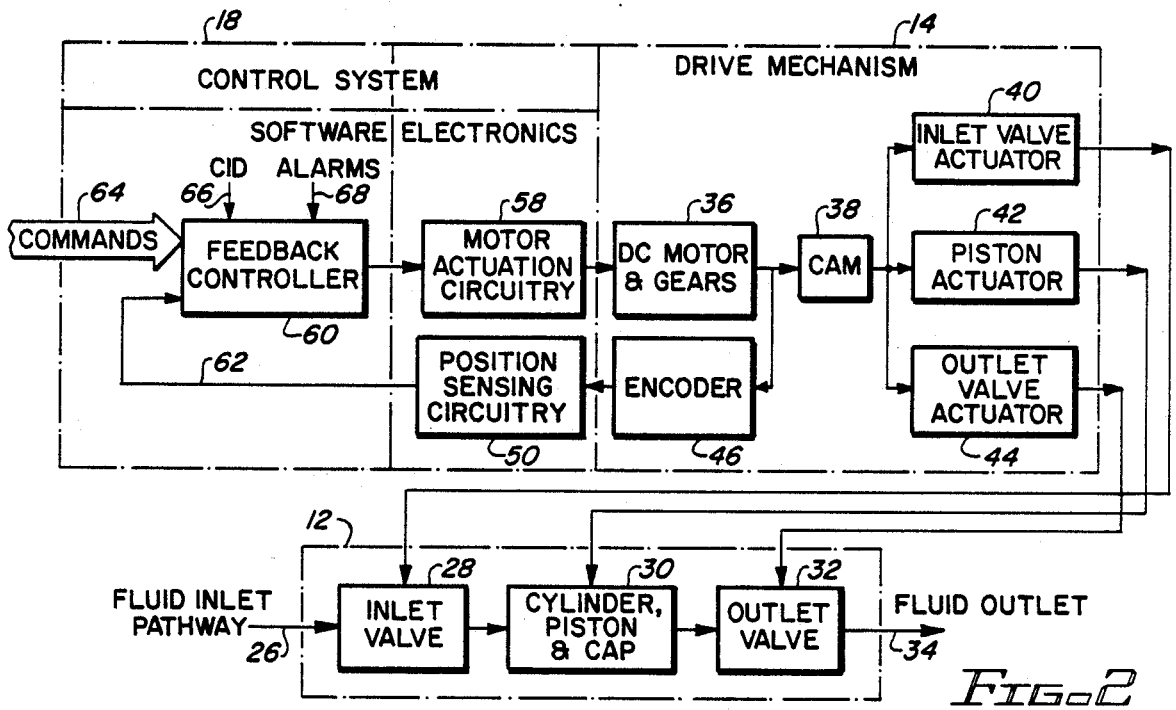
FIG. 2 is a schematic block diagram of the organization of the fluid delivery system.

Further details of drive means 14 and control means 18 are shown in FIG. 2. Disposable fluid pathway and cassette 12 is shown in FIG. 2 as having only a single pumping channel, but in general there will be two or more independent pumping channels. The single pumping channel shown in FIG. 2 comprises a fluid inlet pathway 26 followed by an inlet valve 28; a cylinder, piston, and cap arrangement 30; an outlet valve 32: and a fluid outlet pathway 34.

Drive mechanism 14 comprises a DC motor and gears 36 with a cam 38 on a geared-down output shaft. Cam 38 drives an inlet valve actuator 40, a piston actuator 42, and an outlet valve actuator 44, all of which are mechanically coupled to, respectively, inlet valve 28, a piston in arrangement 30, and outlet valve 32, all in cassette 12. An ironless core DC motor is used in 36. The motor typically has a built-in gear reduction unit to reduce the output speed.

As described in U.S. patent application Ser. No. 07/127,333, entitled "Disposable Cassette for a Medication Infusion System," the end of the motor having the output shaft is mounted onto the top of a drive module chassis at one side thereof with the output shaft extending through the drive module chassis. A drive pulley is mounted on the output shaft and is driven by the motor. A unidirectional bearing is mounted onto the top of the drive module chassis at the other side thereof. The unidirectional bearing supports a drive shaft for rotation therein; both ends of the drive shaft extend from the unidirectional bearing. The unidirectional bearing allows the drive shaft to rotate in one direction only; in the preferred embodiment, the rotation is clockwise when viewed from the top as represented schematically in FIG. 3, for example. A power module cam 38 is mounted on the bottom end of the drive shaft extending from the unidirectional bearing. A drive belt is mounted over the drive pulley and in the groove in the power module cam 38. The motor will thereby drive the power module cam 38 and the drive shaft.

Figure 3:
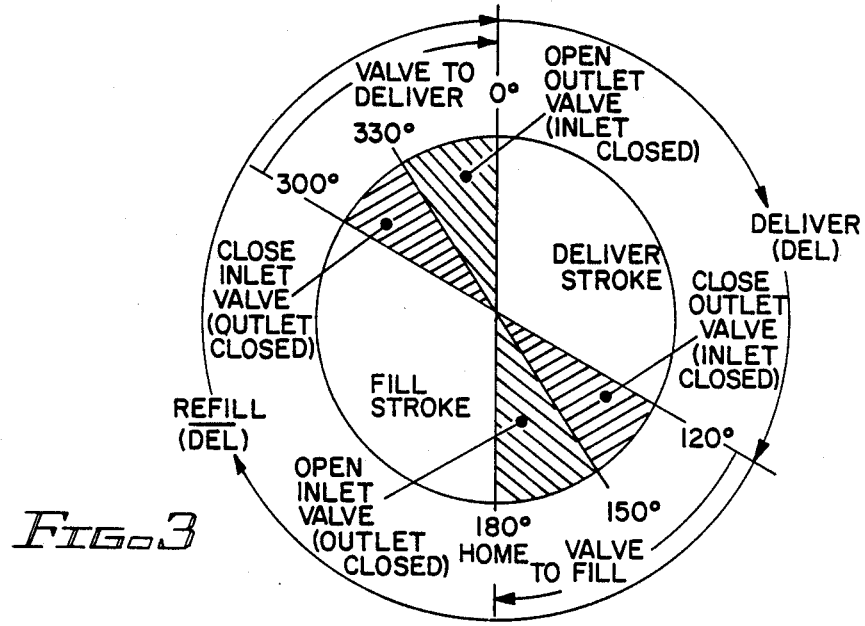
FIG. 3 is a diagram illustrating the different phases of the pumping cycle.

An encoder 46 FIG. 2 provides four types of information necessary for the operation of the pump in cassette 12, as illustrated in FIG. 3. The various segments of the pumping cycle are shown, consisting of a "home" position, a fill stroke segment during which the outlet valve is closed, a delivery stroke segment during which the inlet valve is closed, and two transition segments during which valving is shifted from inlet open/outlet closed to outlet open/inlet closed at the end of the fill stroke segment and back to the initial valving condition at the end of the delivery segment.

Figure 4:
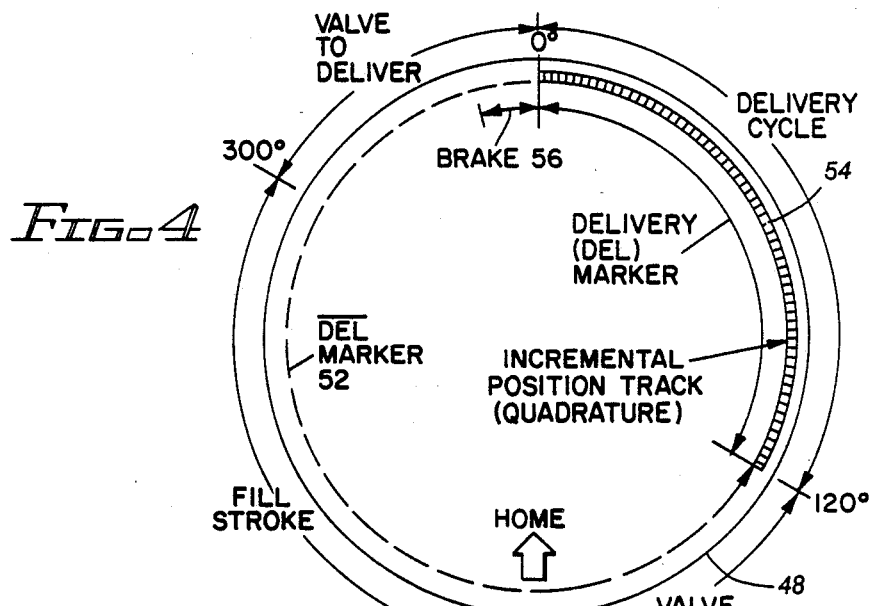
FIG. 4 is a top view of the encoder disk with explanations of the fiducial marks on it.

FIG. 4 is a top view of an encoder disk 48 having fiducial marks on it which are sensed by a position sensor. Encoder disk 48 is fixedly mounted on the top end of the motor drive shaft and rotates with the drive shaft and the cam 38. The position sensor is fixedly mounted above the unidirectional bearing from which the output shaft of the gear reduction unit extends. The position sensor provides position feedback information to a position sensing circuit 50, as shown in FIG. 22. In the preferred embodiment, the position sensor is also capable of direction sensing.

Referring to FIG. 4, the fiducial marks sensed by the position sensor are translated into various electronic signals such as a delivery stroke marker, an incremental delivery marker, and a brake marker. Encoder disk 48 and cam 38 are aligned so that the "home" position is correct. The home position is used to place the cassette piston latch in a known location in order to ensure safe and easy loading of the cassette 12. A delivery marker 52 indicates whether the system is delivering fluid (DEL) or refilling (DEL), (which includes valve-to-fill, fill, and valve-to-deliver). This information is required because the piston must be moved into the cylinder at a controlled rate during the delivery cycle, whereas refilling must be completed as fast as possible to minimize interruption of fluid delivery. The incremental delivery markers 54 are closely spaced along a track on the periphery of the encoder disk 48. The incremental delivery markers 54 are translated into feedback signals for accurate and precise regulation of fluid output flow. When small increments are needed for delivery, it is necessary to stop the motor at the end of the refill cycle. This is accomplished by shorting the motor windings during the interval of the brake marker 56.

Figure 5:
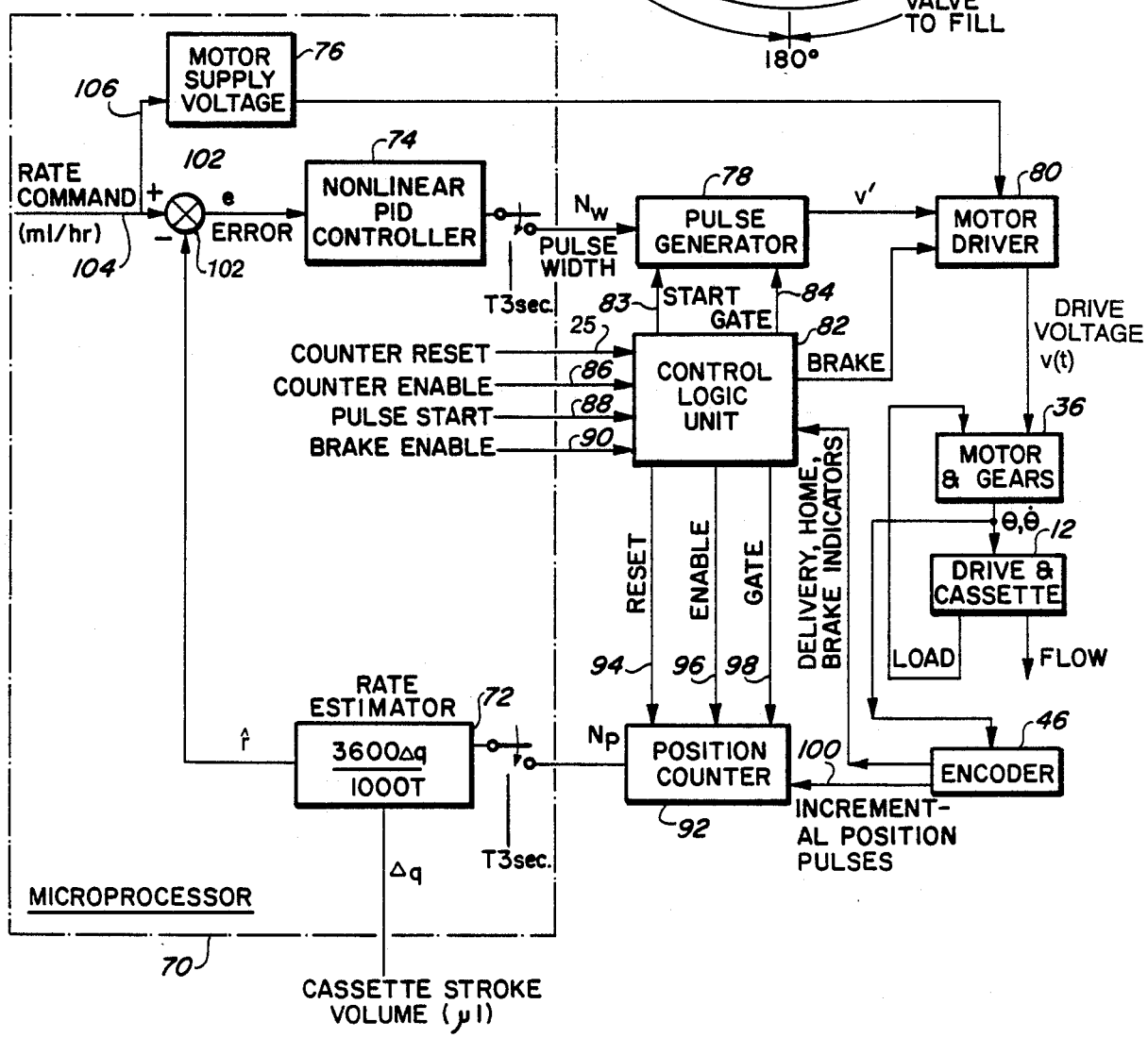
FIG. 5 is a schematic block diagram of a delivery rate control system.

Referring again to FIG. 2, control means 18 is seen to comprise motor actuation circuitry 58, position-sensing circuit 50, and a feedback controller 60. Feedback controller 60 has a position sensing input 62, a command input 64, a cassette identification (CID) input 66, and an alarm input 68. The feedback controller 60 is realized in software. As shown in FIG. 5, a microprocessor 70 comprises a rate estimator 72, a nonlinear controller 74, and a motor supply voltage unit 76.

Motor actuation circuitry 58 comprises a pulse generator 78, a motor driver 80, and a control logic unit 82. Pulse generator 78 is fed an appropriate pulse width by microprocessor 70 via a data bus. Once a pulse width is loaded, microprocessor 70 starts pulse generator 78 via control logic unit 82 through input 83. The output of pulse generator 78 is logic high for the duration of the pulse width, otherwise logic zero. Pulse generator 78 is gated by control logic unit 82 via gate input 84.

Delivery, home, and brake indicators are sent to control logic unit 82 from encoder 46. Inputs to control logic unit 82 from microprocessor 70 include counter reset 85, counter enable 86, pulse start 88, and brake enable 90. Control logic unit 82 is connected to position counter 92 via reset input 94, enable input 96, and gate input 98. Encoder 46 sends incremental position pulses to position counter 92 via input 100.

Microprocessor 70 samples the output of position counter 92 at selected intervals (e.g., three seconds) to determine the amount of fluid delivered. A value for the cassette stroke volume is fed into the rate estimator 72 and together with data from the position counter 92 is used to determine an estimated rate, $r_e$, which is fed into comparator 102. The other input to comparator 102 is a rate command signal 104. Rate command signal 104 also enters the motor supply voltage unit 76 through a parallel connection 106. The input to nonlinear controller 74 is the sampled error signal, e, which is the difference between the rate command, $r_c$, and the estimated rate, $r_e$. Nonlinear controller 74 is an algorithm which adjusts the pulse width based on the error signal. The calculated pulse width count is then transferred to the motor pulse width generator 78.

FIG. 6 is a schematic block diagram of the software procedures making up the implementation of the motor control algorithm for an embodiment in which there are three independent pumping channels. The three sets of motors and their associated gearing 36a, 36b, and 36c are controlled by three distinct software components which cooperate to generate controlled fluid delivery by three pumps. These three software procedures are the infusion control task 108, the motor control task 112, and the pump control timer 110. These three software components will be referred to as the ICT, MCT, and PCT, and are described in more detail below.

DESCRIPTION OF OPERATION

Cassette Loading and Latching:

A loading and latching procedure secures the cassette to the instrument which prepares the system for fluid delivery. To ensure accurate fluid delivery and monitoring, the cassette must be held securely to the face of the instrument and the piston must be held securely by the piston actuator. A cassette slide clamp latches the cassette to the instrument. A piston actuator latch clamps the piston during loading. Based on input signals from sensors that monitor cassette placement and piston latching, the instrument provides a prompt to the operator on setup prior to starting an infusion. There is only one way to install the cassette, and it is easy to remove and re-install.

The loading and latching process does not allow any unintentional delivery of fluid to the patient. Before loading, the cassette slide clamp is closed to occlude the line, and this also opens the cassette hold-down latch. The fluid pathway must be occluded by an outlet valve before the cassette slide clamp is opened during cassette latching. The piston actuator is positioned at the beginning of the fill cycle (home position) prior to loading the cassette. Any movement of the piston fills the cylinder and will not displace fluid to the patient. The microprocessor detects proper cassette placement and piston latching; if a fault occurs, the infusion is stopped and audio and visual alarm signals are produced.

Sensing Proper Cassette Installation:

The instrument electronically detects whether a cassette has been loaded and latched properly. Two sets of sensors do this: the cassette ID sensors and the piston latch-in-place sensor. If a valid ID code is detected and the piston latch is in place, it is assumed that the cassette is properly installed.

The cassette ID sensors identify the cassette characteristics such as stroke volume and detect whether a cassette has been installed. Three emitter/detector pairs located in the instrument sensor bay read the ID code moulded into the cassette body. A three-bit redundant code is used to specify the flow range of the cassette.

The piston latch-in-place (LIP) sensor consists of an emitter/detector pair mounted in the bottom of the sensor module. This sensor detects whether the piston actuator latch has been closed. The LIP sensor is interfaced to the microprocessor by polling an I/O port. The output of the LIP sensor is transformed into a digital logic level by a comparator, and the port is polled at the slowest frequency that does not result in a significantly perceptible delay in the alarm response. The microprocessor periodically checks the latch sensors and issues a hardware fault alarm if a sensor is found to be faulty. The cassette ID code is read by the microprocessor after (1) a change in LIP state occurs, (2) after power is turned on, and (3) after START is pressed. The ID sensors are checked before reading to ensure that they are operating properly. After a cassette has been properly attached, an audio feedback signal is given to the user.

Pump Control:

Several aspects of pump operation are controlled by inputs from the cassette ID and piston latch detectors. If no cassette is installed, the mechanism is homed immediately. If a cassette is installed or partially installed homing is not performed, since this may result in unintentional fluid delivery to the patient. If a cassette has been properly installed, the system is ready for infusion to begin. If a cassette is not installed or latched, a prompt is given if starting the infusion is attempted.

If the pump is infusing, an open piston latch stops the infusion and produces an audio and visual alarm. If the latch is closed again and START pressed, the infusion is started. If the cassette is not sensed, it is assumed that the cassette fell out, and the alarm continues (with a changed message) until it is cleared, which then causes the piston actuator to home.

Fluid Pumping Control:

The range of flow rates is from 0.1 to 999 ml/hr. The keep-vein-open (KVO) rate provides a small increment of fluid at a frequent enough interval to prevent a blood clot from forming on the catheter tip and occluding the line. The minimum time between pulses at minimum flow rate is 15 to 20 seconds. The 90% settling time for infusion rates in response to a step input command is 30 seconds or less. Any fluid delivery which is out of specification for a period of 120 seconds is detected by the system, which then alerts the user. When the pump is not being commanded to infuse, any delivery of fluid gives rise to an immediate alarm. The system detects any single-point sensor failure that would result in erroneous monitoring and control of fluid delivery. The system is failsafe in the event of a sensor failure.

Position Sensing:

Encoder 46 provides position feedback for control of the drive mechanism and cassette. The encoder provides a home position marker at 180° from top dead center for cassette loading. This marker is at the beginning of the fill stroke. A logic signal, DEL, is derived from the encoder that indicates the deliver and refill cycles. The DEL signal is logic one during the delivery cycle, which is from 0° to 120° from top dead center. During the refill cycle, which is from 120° to 360°, the DEL signal is logic zero (DEL). Incremental position markers are provided in the delivery cycle (0° to 120°) for precision feedback control of the fluid delivery rate.

Direction Sensing:

Direction sensing of the drive mechanism is necessary for reasons of safety and accuracy. The drive mechanism includes a mechanical brake which prevents all but a small amount of counter-rotation under mechanical loads and pulse operation. Failure of the anti-backdrive brake is detected by the system. Two quadrature incremental position tracks in the delivery cycle are used for detecting direction. A small amount of backdrive is always possible: this could result in inaccuracies in volume counting or fluid delivered.

Resolution Requirements:

The maximum time between pulses is 18 to 10 seconds. This is important to ensure a small trickle of flow to keep the vascular access site patent. The time required to deliver one stroke of the cassette pump is 3.6 Q/rate, where rate is in ml/hr and Q is the stroke volume in microliters. Dividing by the maximum time desired between pulses yields the number of pulses required per delivery cycle. For example, for an 80 microliter cassette and a rate of 0.1 ml/hr, if the maximum time between pulses is 18 seconds then 160 counts per delivery cycle are required.

Delivery Cycle Incremental Position Counter:

A quadrature counting circuit is included to count encoder pulses during the delivery cycle. The counter is reset at predetermined intervals by the microprocessor after the contents have been read. The output represents the change in angular position of the cam, which is related to the fluid delivery rate. Before it can begin counting, the counter must be enabled by the microprocessor. The counter is gated by the delivery cycle indicator signal, DEL, so that pulses are counted only during the delivery cycle.

Brake Marker:

At low flow rates where small increments of fluid are required, it is necessary to stop the motor at the end of the refill cycle to prevent over-infusion. Stopping the motor is accomplished more quickly by shorting the motor windings. This type of electronic braking makes use of the back EMF generated by the motor. Braking is not used for high infusion rates because overshoot is not a significant problem. The encoder provides a marker at a predetermined angle before the beginning of the delivery cycle that can be used for braking.

Motor Actuation Circuit:

Movement of the drive mechanism and cassette (and subsequent movement of fluid) is controlled by the motor actuation circuit. The motor actuation circuit generates the voltage input to the motor and applies braking when needed. The voltage pulse generated is determined from the rate command, the output of the feedback controller, and the position sensing circuit.

At low rates, during the delivery cycle the drive voltage for the motor consists of a train of pulses. The period of the pulse train is a fixed interval set to 3 seconds and controlled by the microprocessor. At high rates the pulse width is greater than one cycle; i.e., multiple revolutions take place during one pulse width. The pulse width and amplitude are adjusted by the microprocessor to achieve the proper motor speed. The flow produced by the pump is proportional to the motor speed averaged over the pulse period.

The appropriate pulse width is determined by the microprocessor and loaded into the pulse generator circuit via the data bus. Once a pulse width is loaded, the microprocessor starts the pulse generator. The output of the pulse generator is logic high for the duration of the pulse width; otherwise it is logic zero. The pulse width is only measured during the delivery cycle: therefore, the pulse generator is gated by the delivery signal, DEL.

The range of pulse widths is from 1 millisecond to a second. The maximum is 1 second instead of 3 seconds because the delivery cycle is one-third of a revolution; therefore, one-third of the 3-second control period is the delivery cycle pulse width.

A steady-state speed of the motor is proportional to the amplitude of the drive voltage. To simplify the drive circuitry, only two pulse amplitudes are used (5 and 13 volts). Five volts is used for rate commands below 200 ml/hr; otherwise, 13 volts is used.

Refill Cycle

Refilling must be performed as fast as possible in order to minimize the time during which fluid is not delivered to the patient. Refilling is accomplished by loading a pulse width into the pulse generator and starting the motor. The pulse generator is gated by the DEL signal so that no counting takes place during the refill cycle. Refill uses the currently selected drive voltage (5 or 13 volts). Electronic braking is used for flow rates less than a certain set amount. The control logic performs this function when the brake is enabled by the microprocessor.

Homing:

When commanded by the microprocessor to home, the motor voltage is set to 13 volts. When the home position marker on the encoder is detected, the electronic braking is enabled. The cam must be positioned sufficiently close to the home position so that fluid will not be delivered to the patient.

Power Considerations in Multichannel Pump Operation:

In multichannel operation, the leading edges of the pulses for the motors are staggered in order to prevent an excessive peak current drain from the power supply. A transient current increase occurs in the motor circuit when a step increase in voltage is applied. The peak current is approximately the supply voltage divided by the armature resistance, which occurs at the onset of voltage. The current exponentially decays from this value with a time constant of 10 to 20 milliseconds. In four time constants the transient will have decayed 98%, corresponding to 40 to 80 milliseconds.

Feedback Control of Delivery Rate:

Closed-loop feedback control of motor speed (and hence fluid delivery rate) compensates for changes in motor and load characteristics. The input to the control system is the rate command. The output of the system is fluid flow, but since this is not directly observable, an indirect method is used for obtaining the feedback signal. Flow is estimated in the microprocessor from the average rotational speed of the drive, calculated using data from the encoder about delivery cycle incremental position. The difference between the rate command and estimated rate is the error signal. The feedback controller attempts to drive the error signal to zero by adjusting the pulse width using a nonlinear proportional-plus-integral-derivative (nPID) algorithm.

Rate Estimation:

The average fluid delivery rate is estimated using data from the position counter during the delivery cycle. The microprocessor periodically samples the counter to determine the amount of fluid delivered. The sampling period was selected as 3 seconds based on the desired settling time, the need to provide frequent pulsing for rate accuracy and KVO requirements, minimizing the number of calculations required (which minimizes power), and minimizing motor starting and stopping (which adversely affects motor life). Using a single sampling period for all rates also simplifies the software. Since 160 encoder pulses are produced over an 80- microliter delivery stroke, each encoder pulse represents delivery of 0.5 microliter of fluid.

Feedback Controller:

A digital feedback controller determines the motor pulse width required to maintain the estimated rate at the rate command. The input to the controller is the sampled error signal, e, which is the difference between the rate command, $r_c$ and the estimated rate, $r_e$. At predetermined intervals, the controller (a digital computer program) adjusts the pulse width based on the error signal. The calculated pulse width count is then transferred to the motor pulse width generator. The initial pulse width value is determined from open-loop data; this is used to decrease the settling time.

Timing Requirements:

A proper sequence of events in the controller is necessary to ensure closed-loop stability and accuracy. For each pumping channel, the sequence performed at 3-second intervals (the controller sampling period) is given below. This sequence is performed only if the infusion is started and there are no faults detected.

CONTROLLER
Calculate estimated rate, $r_e(kT)$
Read incremental position counter
Reset incremental position counter to zero
Calculate error signal, e(kT)
Calculate change in pulse width output, $\Delta u(kT)$
Sum change with previous output, $\Delta u(kT) + u((k-1)T)$
Limit pulse width output
Store values for next iteration;
i.e. $kT \rightarrow (k-1)T$
Add feedforward compensation increment
Transfer pulse width command to generator
Start motor
END CONTROLLER Software Implementation of Motor Control:

As shown in FIG. 6, three distinct software components, the infusion control task 108, the pump control timer 110, and the motor control task 112 generate controlled fluid delivery to the three motors in the embodiment depicted.

The infusion control task (ICT) coordinates all aspects of fluid delivery to the three pumps. This software block is told when to start or stop an infusion, and it responds accordingly. It also monitors the course of the infusion and informs the system of any alarms (air in line, occlusion, etc.) or when the infusion is complete. The ICT does not directly control the motors; it merely decides when each motor should begin and end delivery of fluid, or when the infusion rate should change. When an infusion is to begin, stop, or change rate, the ICT sends a message to either the pump control timer or the motor control task to perform the actual details. The ICT keeps track of the state of each pump by maintaining a state variable. This state variable can have the values "READY", "HOMING", "INFUSING", etc.

The pump control timer is a procedure which executes at regular intervals, performing various monitoring functions for the ICT and MCT. The PCT also generates the messages to the motor control task at three-second intervals which cause closed-loop control of each pump to occur. The PCT executes every 60 milliseconds. This interval provides the basic clock that controls all motor control timing. The choice of 60 milliseconds was influenced by several considerations. Part of the job of the PCT is to monitor the DEL signal from the encoder. Assuming a maximum motor speed of five revolutions per second, a delivery cycle can occur in 67 milliseconds. Therefore, the timer must sample the DEL signal at least this frequently. The control interval for closed-loop motor control was chosen to be three seconds. Since the PCT provides the basic timing for the motor control task, the PCT must execute at a frequency which is a factor of three seconds, i.e. 3000 milliseconds must be an integral multiple of the timing frequency of the pump timer. To reduce peak current demands, the starting of each motor must be staggered so that the commands to start two motors are no closer together than 25 milliseconds. The operating system clock operates at an interval of 20 milliseconds, so that all timer routines must be an integral multiple of 20 milliseconds. Finally, the timer must operate at as low a frequency as possible to reduce the workload on the microprocessor and thereby reduce power consumption.

Every 60 milliseconds, the instrument operating system causes the PCT to execute. The PCT routine performs two types of functions: (1) general motor position dependent monitoring of all three pumps. This requires checking the DEL signal on each pump to determine whether each pump is in a fill or delivery cycle. Appropriate functions (unrelated to motor control timing) such as encoder checks and VR/VI/TVI updating are then performed. The timer then determines which of the pumps requires more handling. At each 60 millisecond execution, the timer routine goes through the next step in a five-part cycle. Steps 1 through 3 causes special processing to be performed for pumps a, b and c. Steps 4 and 5 are null operations (no further processing is performed by the PCT). FIG. 7 shows the PCT timing.

Since the special processing for each pump occurs only in one of five pump control executions, each pump processing occurs at 300 millisecond intervals and the processing between pumps is at least 60 milliseconds. This 60-millisecond gap between pump processing prevents pumps from starting at the same instant. The special processing that occurs every 300 milliseconds for each pump consists of checking the state variable for the pump, monitoring appropriate signals, and generating messages to the ICT and/or MCT where needed.

The motor control task (MCT) handles the job of running the motors so that fluid is delivered at a prescribed rate. The MCT can be instructed to perform various functions by reception of the following messages: (a) "perform open-loop control on pump X"—the MCT responds to this instruction by sending one pulse to the motor at a "best guess" voltage and pulse width, so that pump X will deliver fluid at approximately the prescribed rate for the following three seconds. This message is used to initiate fluid delivery or change rates on pump X. (b) "perform closed-loop control on pump X"—the MCT is given an estimate of how fast the motor has been running over the last three seconds. The MCT uses this information to determine the size of the next pulse to put out to the motor to maintain the prescribed fluid rate. (c) "stop pump X"—the MCT sets up the motor control software so that the motor is stopped. (d) "home pump X"—the PCT generates the signals necessary to cause the motor to move to the home position.

Operational Sequences:

The following sequences of events occur in response to various infusion control commands:

Start infusion on pump X—see FIG. 8. The ICT sets the state of the motor to START RUN. At the next execution of the PCT at which the pump control processing for pump X is performed, a "perform open-loop control on pump X" message is sent to the MCT. The state variable is set to RUNNING. The PCT sets up a counter so that every three seconds the estimated rate of the motor for pump X is calculated and a "perform closed-loop on pump X" message to the MCT is generated.

Stop infusion on pump X—the ICT sends a "stop pump X" message to the MCT. The ICT sets the state of pump X to STOPPING so that the PCT does not generate any more "perform closed-loop control on pump X" messages.

Change rate on pump X—see FIG. 9. The ICT sends a "perform open-loop control on pump X" message directly to the MCT. After the MCT executes the open-loop control procedure, the motor for pump X will run open-loop until the MCT receives the next message from the PCT directing the MCT to perform closed-loop control.

Home pump X—the ICT sends a "home pump X" message directly to the MCT and sets the state of pump X to HOMING. The MCT begins the homing sequence. The PCT, noting that pump X state is homing, will watch the motor position. When the motor reaches home, the pump state variable is set to NO SET (homing is only performed when no cassette is in place).

Although there have been described above specific arrangements of a fluid delivery control and monitoring apparatus for a medication infusion system for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A fluid delivery monitoring and control apparatus for use in a medical infusion system employing a disposable fluid pathway and cassette, which cassette contains a plurality of fluid channels, each of which includes a positive displacement pump having a piston mounted for reciprocating movement within a chamber and respective intake and outlet valves for controlling fluid flow through said chamber, the apparatus comprising:
   drive means for coupling to a cassette in association with a selected fluid channel including means for actuating said piston and said intake and outlet valves in a controlled sequence;
   encoding means coupled to the drive means for providing signals indicative of home position and rate of movement of said drive means;
   means for receiving rate command signals defining a desired rate of fluid flow through an associated cassette;
   means for ascertaining fluid flow rate from rate of movement signals and from cassette indicia indicating piston stroke volume and generating feedback signals indicative of sensed flow rate; and
   means for combining the rate command signals with said feedback signals to develop signals for controlling the drive means.

2. The apparatus of claim 1 further including control means coupled to receive said developed control signals including a pulse generator coupled to apply variable width drive pulses to said drive means and a pulse width controller coupled to control the pulse generator to generate drive pulses of a selected width corresponding to signals from the combining means.

3. The apparatus of claim 2 further including means to vary the amplitude level of said rive pulses between at least HIGH and LOW voltage levels in accordance with said rate command signals.

4. The apparatus of claim 3 further including means for selecting a HIGH voltage level for activating the drive means during movement of the piston to a home position.

5. The apparatus of claim 2 wherein the fluid flow rate ascertaining means comprise a pulse counter responsive to signals from the encoding means and means for inhibiting the pulse counter from counting pulses except when the cassette piston is delivering fluid through the outlet valve.

6. The apparatus of claim 2 wherein the encoding means further provide a logic signal distinguishing between delivery and non-delivery modes of the associated cassette fluid channel, the apparatus further including means for controlling the pulse generator to apply said variable width drive pulses to the drive means only during actuation in the delivery mode.

7. The apparatus of claim 6 wherein said pulse generator is coupled to activate said drive means continuously for a fill stroke interval which is within the duration of the non-delivery mode.

8. The apparatus of claim 1 wherein said controlled sequence consists of, beginning at a home position in which the inlet valve is open and the outlet valve is closed, actuating the piston through a fill stroke, closing the inlet valve, opening the outlet valve, actuating the piston in accordance with said developed signals through a delivery stroke, closing the outlet valve and opening the inlet valve.

9. The apparatus of claim 8 further including means for selectively braking said drive means.

10. The apparatus of claim 9 wherein said braking means is adapted to apply electronic braking to the drive means for a predetermined interval preceding actuation of said piston to deliver fluid for rates of fluid flow which are less than a selected threshold level.

11. The apparatus of claim 10 wherein the braking means is further adapted to apply electronic braking to the drive means upon receiving a signal indicative of home position from the encoding means.

12. The apparatus of claim 1 wherein said encoding means comprise a disk mounted to rotate with said drive means, said disk having a plurality of indicia located at selected points about its periphery for indicating rate of movement of the drive means.

13. The apparatus of claim 12 wherein said disk includes a fiducial mark indicative of home position.

14. The apparatus of claim 5 further including means for sampling the pulse counter at repetitive intervals and concurrently applying signals developed by the combining means to control the pulse generator at the same repetitive intervals.

* * * * *